United States Patent
Luciano et al.

(10) Patent No.: US 9,011,378 B2
(45) Date of Patent: Apr. 21, 2015

(54) DEVICE FOR INCREASING CEREBRAL BLOOD FLOW

(75) Inventors: Mark G. Luciano, Highland Heights, OH (US); Stephen M. Dombrowski, University Heights, OH (US); Timothy Moran, University Heights, OH (US)

(73) Assignees: The Cleveland Clinic Foundation, Cleveland, OH (US); CSF Therapeutics, Cleveland, OH (US)

( * ) Notice: Subject to any disclaimer, the term of this patent is extended or adjusted under 35 U.S.C. 154(b) by 159 days.

(21) Appl. No.: 12/770,276

(22) Filed: Apr. 29, 2010

(65) Prior Publication Data

US 2011/0004158 A1    Jan. 6, 2011

Related U.S. Application Data

(63) Continuation of application No. PCT/US2008/012355, filed on Oct. 31, 2008.

(60) Provisional application No. 61/001,795, filed on Nov. 2, 2007.

(51) Int. Cl.
*A61M 5/142* (2006.01)
*A61M 27/00* (2006.01)
(Continued)

(52) U.S. Cl.
CPC .......... *A61M 27/002* (2013.01); *A61M 5/14224* (2013.01); *A61M 5/14593* (2013.01); *A61M 2210/0693* (2013.01); *A61M 2210/1003* (2013.01); *F04B 43/06* (2013.01); *A61M 27/006* (2013.01)

(58) Field of Classification Search
USPC ............... 604/31, 65–67, 131–133, 151, 153, 604/503–506
See application file for complete search history.

(56) References Cited

U.S. PATENT DOCUMENTS

| | | |
|---|---|---|
| 4,460 A | 4/1846 | Beach |
| 4,519,403 A | 5/1985 | Dickhudt |

(Continued)

FOREIGN PATENT DOCUMENTS

| | | |
|---|---|---|
| DE | 299 21 166 U1 | 4/2000 |
| EP | 0 808 184 B1 | 11/1997 |

(Continued)

OTHER PUBLICATIONS

Dombrowski, S.M., et al., "Chronic Hydrocephalus-Induced Changes in Cerebral Blood Flow: Mediation Through Cardiac Effects," *J. Cereb Blood Flow Metab.*, 26:1298-1310 (Feb. 22, 2006).

(Continued)

*Primary Examiner* — Nathan R Price
(74) *Attorney, Agent, or Firm* — Hamilton, Brook, Smith & Reynolds, P.C.

(57) ABSTRACT

A device for regulating cerebrospinal fluid in a cerebrospinal fluid space includes a cerebrospinal conduit having a distal end for insertion into the cerebrospinal fluid space in fluid communication with the cerebrospinal fluid. An actively oscillatably changeable sealed fluid volume can be in fluid communication with the cerebrospinal conduit. The changeable sealed fluid volume can be in a sealed fluid path extending to the distal end of the cerebrospinal conduit and is capable of actively oscillating in a changing fluid volume size for oscillating the cerebrospinal fluid in and out of the distal end of the cerebrospinal conduit and cerebrospinal fluid space.

13 Claims, 6 Drawing Sheets

(51) Int. Cl.
  *A61M 5/145* (2006.01)
  *F04B 43/06* (2006.01)

(56) References Cited

U.S. PATENT DOCUMENTS

| | | | |
|---|---|---|---|
| 4,686,085 | A | 8/1987 | Osterholm |
| 4,767,400 | A | 8/1988 | Miller et al. |
| 5,084,016 | A | 1/1992 | Freeman et al. |
| 5,399,166 | A * | 3/1995 | Laing ............... 604/146 |
| 5,529,214 | A * | 6/1996 | Lasonde et al. ........... 222/105 |
| 5,693,989 | A | 12/1997 | Satomi et al. |
| 5,711,507 | A | 1/1998 | Berget et al. |
| 5,957,912 | A | 9/1999 | Heitzmann |
| 5,980,480 | A | 11/1999 | Rubenstein et al. |
| 6,105,582 | A | 8/2000 | Pranevicius |
| 6,683,066 | B2 | 1/2004 | Wang |
| 7,972,305 | B2 * | 7/2011 | Mittermeyer ............ 604/132 |
| 2003/0167031 | A1 | 9/2003 | Odland |
| 2003/0236442 | A1 | 12/2003 | Connors et al. |
| 2005/0187430 | A1 | 8/2005 | Aundal et al. |
| 2006/0200083 | A1 * | 9/2006 | Freyman et al. ............. 604/181 |
| 2006/0271022 | A1 * | 11/2006 | Steinbach et al. ......... 604/891.1 |
| 2009/0177279 | A1 | 7/2009 | Luciano et al. |

FOREIGN PATENT DOCUMENTS

| | | |
|---|---|---|
| EP | 1 676 527 A1 | 7/2006 |
| WO | WO 98/02202 A1 | 1/1998 |
| WO | WO 99/07276 A2 | 2/1999 |
| WO | WO 01/39819 A2 | 6/2001 |
| WO | WO 2007/014028 A1 | 2/2007 |
| WO | WO 2009/058353 A1 | 5/2009 |

OTHER PUBLICATIONS

Egnor, M. et al., "A Model of Intracranial Pulsations," *Pediatr. Neurosurg.*, 35(6):284-298 (Dec. 2001).
Egnor, M. et al., "A Model of Pulsations in Communicating Hydrocephalus," *Pediatr. Neurosurg.*, 36(6):281-303 (Jun. 2002).
Egnor, M. et al., "Resonance and the Synchrony of Arterial and CSF Pulsations", *Pediatr, Neurosurg.*, 38:273-276 (2003).
Fukuhara, T., et al., "Effects of Ventriculoperitoneal Shunt Removal on Cerebral Oxygenation and Brain Compliance in Chronic Obstructive Hydrocephalus," *J Neurosurg,*. 94(4):573-581 (Apr. 2001).
Greitz, D., "Radiological Assessment of Hydrocephalus: New Theories and Implications for Therapy", *Neurosurg, Rev.*, 27:145-165 (May 26, 2004).
Greitz, D., "The Hydrodynamic Hypothesis Versus the Bulk Flow Hypothesis," *Neurosurg. Rev.*, 27:299-300 (Jul. 23, 2004).
Heymann, M.A., et al., "Blood Flow Measurements With Radionuclide-Labeled Particles", *Prog. Cardiovasc. Dis.*, 20(1):55-79 (Jul.-Aug. 1977).
Johnson, M.J., et al., "Development and Characterization of an Adult Model of Obstructive Hydrocephalus," *J. Neurosci Methods*, 91:55-65, (1999).
Luciano, M.G., et al., "Cerebrovascular Adaptation in Chronic Hydrocephalus," *J. Cereb. Blood Flow Metab.*, 21(3):285-294 (2001).
Notification of Transmittal of the International Search Report and the Written Opinion of the International Searching Authority, or the Declaration from PCT/US2008/012355 mailed Feb. 10, 2009.
Notification of Transmittal of the International Preliminary Report on Patentability from PCT/US2008/012355 mailed May 14, 2010.

* cited by examiner

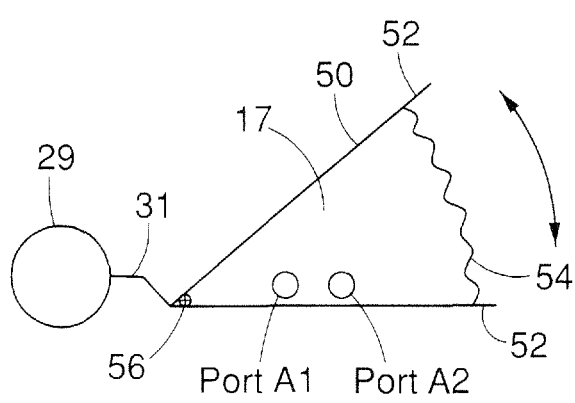
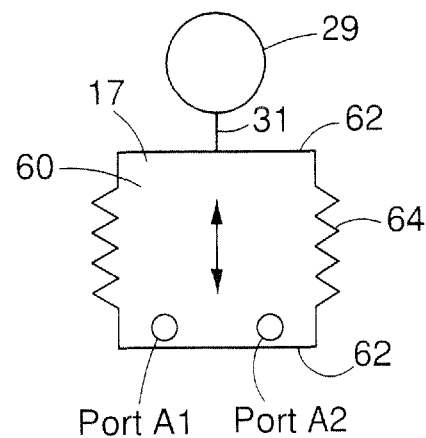
FIG. 6  FIG. 7
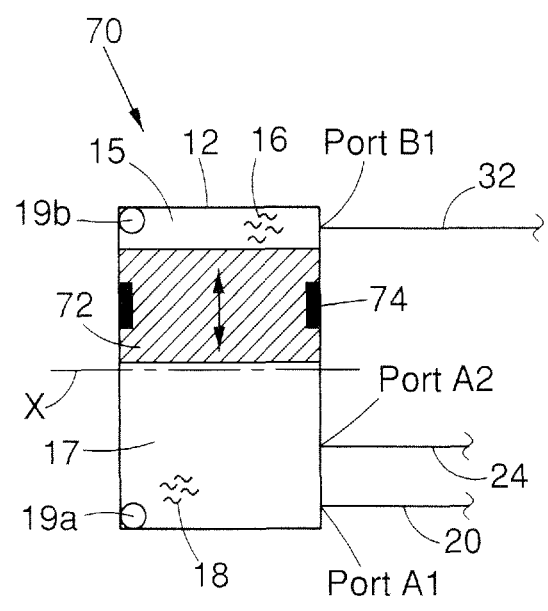
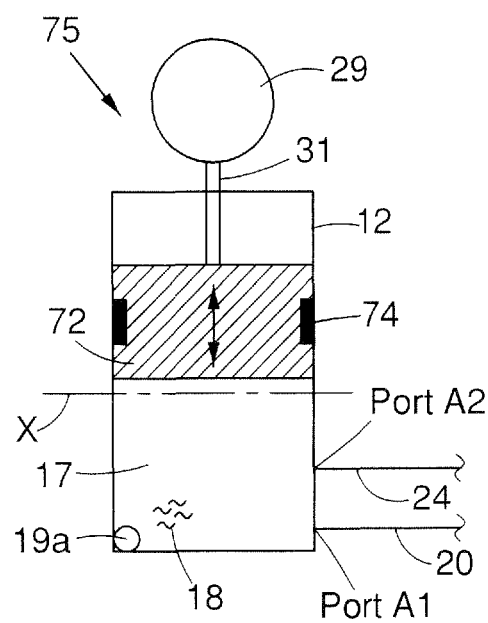
FIG. 8  FIG. 9

DEVICE FOR INCREASING CEREBRAL BLOOD FLOW

RELATED APPLICATIONS

This application is a continuation of International Application No. PCT/US2008/012355, which designated the United States and was filed Oct. 31, 2008, published in English, which claims the benefit of U.S. Provisional Application No. 61/001,795, filed on Nov. 2, 2007. The entire teachings of the above applications are incorporated herein by reference.

BACKGROUND

It has been determined that the cerebrospinal fluid (CSF) environment of the brain is important in regulating, in a negative and positive fashion, cerebral blood flow. Control of the pressure and flow pulsatility of CSF can result in improved blood flow in the brain secondary to decreasing cerebrovascular resistance and increasing cranial compliance. In many situations involving brain injury, whether due to stroke, trauma or other causes, a major effort in an intensive care unit (ICU) setting is to prevent secondary, extended brain injury which results from ischemia caused by decreased cerebral blood flow. These efforts can involve increasing systemic arterial pressure, or decreasing intracranial pressure (ICP) to ultimately increase cerebral perfusion. In the case of trauma and stroke for example, large hemi-craniotomies have been performed to decrease intracranial pressure and increase brain compliance allowing more blood flow. Another alternative is the placement of a ventricular catheter to allow drainage of cerebral spinal fluid, allowing more space for blood inflow and increasing brain compliance. Unfortunately, the former technique is a large procedure and has complications. Ventricular catheterization is limited by the amount of fluid which can be drained, also resulting in slit ventricles completely drained without further advantage.

SUMMARY

The present invention can provide a device for regulating cerebrospinal fluid in a cerebrospinal fluid space including a cerebrospinal conduit having a distal end for insertion into the cerebrospinal fluid space in fluid communication with the cerebrospinal fluid. An actively oscillatably changeable sealed fluid volume can be in fluid communication with the cerebrospinal conduit. The changeable sealed fluid volume can be in a sealed fluid path extending to the distal end of the cerebrospinal conduit and is capable of actively oscillating or modulating in a changing fluid volume size for oscillating or modulating the cerebrospinal fluid in and out of the distal end of the cerebrospinal conduit and cerebrospinal fluid space.

In particular embodiments, the device can include an actuator coupled to the changeable sealed fluid volume for oscillating the changing fluid volume size of the changeable sealed fluid volume. A sensor system can sense conditions of a patient. The sensor system can be in communication with the actuator for controlling operation of the actuator. The sensor system can include a control system for controlling operation of the actuator. Operation of the actuator can be synchronized with a biorythm of the patient. The biorythm can be related to the patient's heart. The actuator can be synchronized with a signal such as an ECG signal, a pulse signal and a pressure signal. The sensor system can include a sensor for sensing within the cerebrospinal fluid space for forming a feed back loop to control the level of cerebrospinal fluid within the cerebrospinal fluid space. A fluid storage container can be coupled to the changeable sealed fluid volume and controllably fluidly isolated from the changeable sealed fluid volume. In one embodiment, the changeable sealed fluid volume can include a movable piston, and in another embodiment, a bellows device. In other embodiments, the changeable sealed fluid volume can include a deformable fluid tight membrane on which the actuator is capable of applying an oscillating force for oscillating the changing fluid volume size of the changeable sealed fluid volume. The changeable sealed fluid volume can be within a container. The container can have a deformable fluid tight membrane with a first surface that defines a boundary forming at least a portion of the changeable sealed fluid volume. The deformable membrane is capable of deforming to oscillate the changing fluid volume size of the changeable sealed fluid volume. The deformable membrane can have a second surface which is fluidly isolated from the first surface. Application of an oscillating force on the second surface of the deformable membrane is capable of deforming the deformable membrane to oscillate the changing fluid volume size of the changeable sealed fluid volume. The container can have a first port in communication with the changeable sealed fluid volume. The cerebrospinal conduit can be coupled to the first port. The container can also have a second port in communication with the second surface of the deformable membrane. In one embodiment, the deformable membrane can be a diaphragm extending within the container. In another embodiment, the deformable membrane can be a balloon positioned within the container. An oscillating pump can be coupled to the second port of the container for providing oscillating fluid pressure to the second surface of the deformable membrane.

The present invention can also provide a device for regulating cerebrospinal fluid in a cerebrospinal fluid space including a cerebrospinal conduit having a distal end for insertion into the cerebrospinal fluid space in fluid communication with the cerebrospinal fluid. An actively oscillatably changeable sealed fluid volume can be in fluid communication with the cerebrospinal conduit. The changeable sealed fluid volume can be in a sealed fluid path extending to the distal end of the cerebrospinal conduit and is capable of actively oscillating or modulating in a changing fluid volume size for oscillating or modulating the cerebrospinal fluid in and out of the distal end of the cerebrospinal conduit and cerebrospinal fluid space. An actuator can be coupled to the changeable sealed fluid volume for oscillating the changing fluid volume size of the changeable sealed fluid volume. A control system can control operation of the actuator and can be synchronized with a biorythm.

The present invention also provides a method of regulating cerebrospinal fluid in a cerebrospinal fluid space. A distal end of a cerebrospinal conduit can be inserted into the cerebrospinal fluid space in fluid communication with the cerebrospinal fluid. An actively oscillatably changeable sealed fluid volume can be coupled in fluid communication with the cerebrospinal conduit. The changeable sealed fluid volume can be in a sealed fluid path extending to the distal end of the cerebrospinal conduit. The changeable sealed fluid volume can be actively oscillated or modulated in a changing fluid volume size for oscillating or modulating the cerebrospinal fluid in and out of the distal end of the cerebrospinal conduit and cerebrospinal fluid space.

In particular embodiments, the changing fluid volume size of the changeable sealed fluid volume can be oscillated with an actuator coupled to the changeable sealed fluid volume. Conditions of a patient can be sensed with a sensor system. The sensor system can be in communication with the actuator for controlling operation of the actuator. Operation of the actuator can be controlled with a control system associated with the sensor system. The actuator can be operated in synchronization with a biorythm of the patient. The biorythm can be related to the patient's heart. The actuator can be synchronized with a signal such as an ECG signal, a pulse signal and a pressure signal. The level of cerebrospinal fluid within the cerebrospinal fluid space can be controlled with a sensor within the cerebrospinal fluid space that forms a feed back loop. A fluid storage container can be coupled to the changeable sealed fluid volume. The fluid storage container can be controllably fluidly isolated from the changeable sealed fluid volume. In one embodiment, the changing fluid volume size of the changeable sealed fluid volume can be oscillated with a movable piston, and in another embodiment, with a bellows device. In other embodiments, the changeable sealed fluid volume can include a deformable fluid tight membrane. An oscillating force can be applied on the deformable membrane for oscillating the changing fluid volume size of the changeable sealed fluid volume. The changeable sealed fluid volume can be within a container. The container can have a deformable fluid tight membrane with a first surface that defines a boundary forming at least a portion of the changeable sealed fluid volume. The deformable membrane can be deformed to oscillate the changing fluid volume size of the changeable sealed fluid volume. The deformable membrane can have a second surface which is fluidly isolated from the first surface. An oscillating force can be applied on the second surface of the deformable membrane for deforming the deformable membrane to oscillate the changing fluid volume size of the changeable sealed fluid volume. The container can have a first port in communication with the changeable sealed fluid volume, and a second port in communication with the second surface of the deformable membrane. The cerebrospinal conduit can be coupled to the first port. In one embodiment, a diaphragm can be extended within the container as the deformable membrane. In another embodiment, a balloon can be positioned within the container as the deformable membrane. Oscillating fluid pressure can be provided to the second surface of the deformable membrane with an oscillating pump coupled to the second port of the container.

The present invention can provide use of a device including a cerebrospinal conduit having a distal end for insertion into a cerebrospinal fluid space in fluid communication with a cerebrospinal fluid. An actively oscillatably changeable sealed fluid volume can be in fluid communication with the cerebrospinal conduit. The changeable sealed fluid volume can be in a sealed fluid path extending to the distal end of the cerebrospinal conduit and is capable of actively oscillating or modulating in a changing fluid volume size for oscillating or modulating the cerebrospinal fluid in and out of the distal end of the cerebrospinal conduit and cerebrospinal fluid space for regulating the cerebrospinal fluid in the cerebrospinal fluid space.

In embodiments of the present invention, through alteration of CSF space volume in a cardiac synchronous manner, intracranial pressure and flow pulsation can be controlled and cranial compliance and cerebrovascular impedent be changed. Embodiments of the present invention device can be used, for example, in a patient with a decreased cerebral blood flow in an ICU setting and, who can also be candidate for other CSF space catheterization to an external bag. The device can be part of an externalized catheter and bag system and no further invasive procedure is needed. The device can maintain the closed CSF drainage system and allow CSF removal as needed.

Embodiments of the device can be used to increase cerebral blood flow in patients with elevated intracranial pressure, and can be used in a patient (e.g., an ICU patient) who is undergoing external CSF drainage using, for example, a standard ventricular catheter or any other catheterization of a CSF space. It may be used in patients with a variety of decreased cerebral blood flow states including those induced by trauma, stroke, vasospasm, hydrocephalus or congestive heart failure. It can be applied as a device connected to a standard external ventricular drainage catheter and integrated between the standard catheter and a standard external drainage bag.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 6 is a schematic drawing of another embodiment of an oscillating sealed fluid volume.

FIG. 7 is a schematic drawing of yet another embodiment of an oscillating sealed fluid volume.

FIGS. 8 and 9 are schematic drawings of still other embodiments of oscillating sealed volumes.

DETAILED DESCRIPTION

Figure 1:
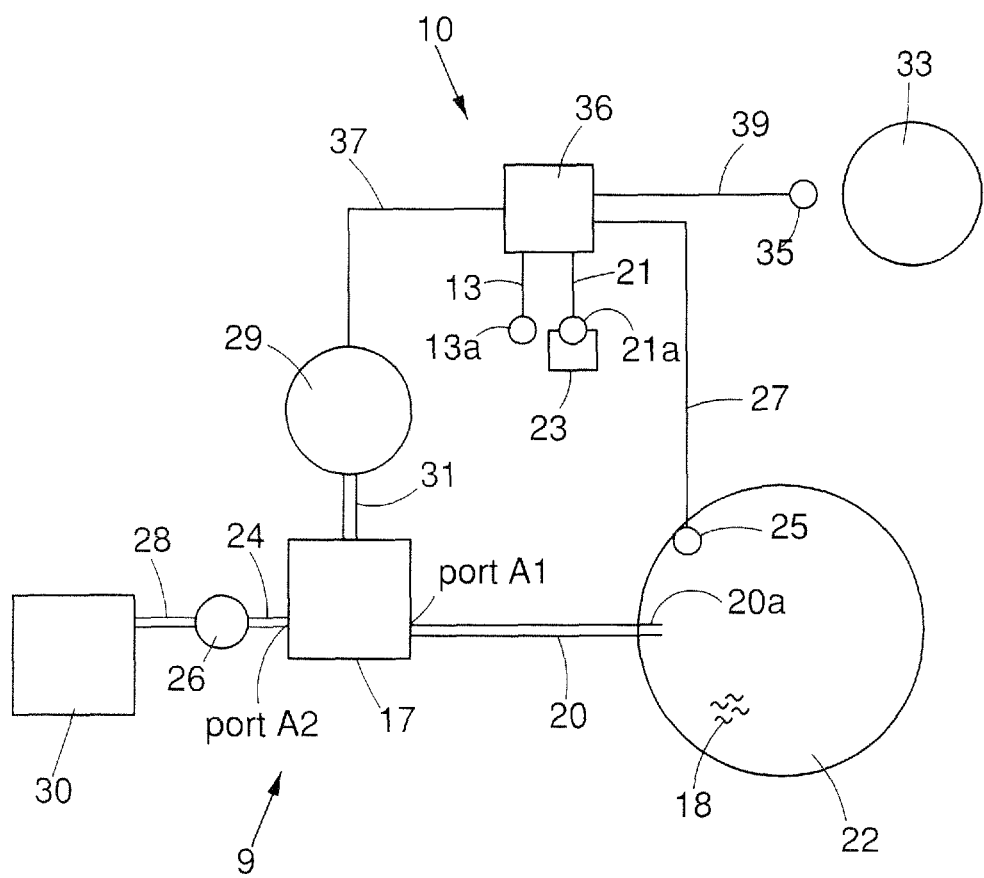
FIG. 1 is a schematic drawing of an embodiment of a device or system for regulating cerebrospinal fluid.

Referring to FIG. 1, in one embodiment of the present invention, cerebrospinal fluid regulating device or system 10, can regulate cerebrospinal fluid 18 within a cerebrospinal fluid space or volume 22, such as in the head or spine of a patient. Device 10 can include a cerebrospinal conduit or catheter 20, which has an open distal end 20a that can be inserted into the cerebrospinal fluid space 22. The cerebrospinal catheter 20 is an fluid communication with an actively oscillatably changeable sealed fluid supply, reservoir, chamber or volume 17 via port A1. A drainage or storage container or bag 30 can be connected to the volume 17 via port A2 by a conduit or tube 24, a valve 26, and a conduit or tube 28. The valve 26 can be a 3-way stopcock, or other suitable shut off valve device or member, manual or automatically controlled, and in some embodiments can be a clamp. The valve 26 can be opened to allow drainage of cerebrospinal fluid 18 from the cerebrospinal fluid space 22, and into the drainage bag 30 via catheter 20 and volume 17. Once the valve 26 is closed, the volume 17 is isolated from or sealed off from fluid communication with the drainage bag 30 and is in sealed fluid communication with the catheter 20, and the cerebrospinal fluid 18 therein.

The volume 17 can be oscillated or modulated by an actuator 29 that is connected or coupled to volume 17 by a coupling member 31. The volume 17 can be fluid and biologically sealed tight relative to the actuator 29. The actuator 29 can be a pump such as a piston, rotary, centrifugal, peristaltic, roller pump, etc., or a rotary or linear actuator, and can apply or cause forces or pressure on the volume 17 for changing the fluid volume size of the volume 17. In some embodiments, the actuator 29 and volume 17 can be separate units, and in other embodiments, one unit. Since the volume 17 is in a sealed fluid communication path extending through catheter 20 to the cerebrospinal fluid space 22, a change in size to be a smaller fluid volume size can force cerebrospinal fluid 18 from or within the volume 17 and catheter 20 fluid path, into cerebrospinal fluid space 22. A change in size of volume 17 to be a larger fluid volume size, can draw cerebrospinal fluid 18 from the cerebrospinal fluid space 22 into the volume 17 and catheter 20 fluid path. The actuator 29 can be oscillated or modulated to oscillate or modulate the volume 17, which in turn can oscillate or modulate cerebrospinal fluid 18 in and out of the distal end 20a of the catheter 20 and the cerebrospinal fluid space 22, which can oscillate or modulate fluid pressure therein. Such oscillation or modulation can be slow or periodic, to increase or decrease pressure in the cerebrospinal fluid space 22 for long periods of time, for example, hours, days, or weeks, or can be multiple or many times per minute on a continual basis. Drawing cerebrospinal fluid 18 from the cerebrospinal fluid space 22 can reduce pressure in the cerebrospinal fluid 22 and can increase blood flow, for example cerebral blood flow.

The actuator 29 and volume 17 can be oscillated or modulated continuously in synchronization with aspects, conditions or biorhythms of a patient to aid, assist or increase blood flow. Examples of some biorhythms can be heart rate, cardiac cycle, blood pressure pulse, breathing or respiratory rate. The actuator 29 can be connected to and controlled by signals from a monitor or controller 36 via a control line 37, which can be a physical electrically connected line, or a wireless connection. The monitor 36 can have a sensor 35 connected by a control line 39 (wireless connection or physical electrical line) which can monitor a patient's biorhythm source 33, for example, the heart. In one embodiment, the monitor or controller 36 can be or include an electrical cardiogram (ECG or EKG) monitor for monitoring heart rate or heart activity. The actuator 29 and volume 17 can be oscillated in synchronization with the heart and/or related electrical signals to increase blood flow. Oscillation of the cerebrospinal fluid 18 can increase and decrease pressure in the cerebrospinal fluid 22 in an alternating manner, which can allow blood to flow more easily through blood vessels around or near cerebrospinal fluid space 22. The alternating pressure can in some cases form a sort of pumping action. In another embodiment, the monitor or controller 36 can be or include an intra-cranial pressure monitor which can be connected by a control line 27 (wireless or physical) to a sensor 25 in or near the cerebrospinal fluid space 22, for sensing pressure in or around the cerebrospinal fluid space 22 and providing related electrical signals, thereby enabling sensing of the rhythm or timing of blood flow in the region. Sensor 25 can be an intracranial sensor, and can act as a blood pulse sensor or a fluid pressure sensor. The sensor 25 can be part of a feed back loop for controlling actuator 29 and controlling the pressure or fluid level within the cerebrospinal fluid space 22 to a desired level. Some embodiments can include a pressure sensor 13a for measuring blood pressure, which can be connected to monitor or controller 36 by a wireless or physical line 13. In addition, an attachable pulse sensor 21a for attaching to appendages or other suitable body parts, such as a finger, toe, or ear pulse sensor, can be included for measuring blood pressure pulses from a body part or appendage 23 such as a finger, toe or ear. The sensor 21a can be connected to monitor or controller 36 by a wireless or physical line 21. In particular embodiments, cerebrospinal fluid 18 can be removed from the cerebrospinal fluid space 22 during systole to decrease intracranial pressure when blood flow is maximum, and deliver the cerebrospinal fluid 18 into the cerebrospinal fluid space 22 during diastole. Such a pumping action can be tied to the heart or heart beat, and synchronized with the ECG or EKG, blood pressure pulse, or signals associated therewith, or other signals tied o the cardiac cycle.

In some embodiments, the monitor or controller 36 and/or actuator 29 can include controls or software that can control the frequency, timing and duration of the operation of the actuator 29 to form a desired oscillating or modulating waveform depending upon the biorhythm sensed, its sensing location, or user input. For example, when the actuator 29 is a pump, there can be a delay between the pumping action waveform and the waveform of a biorhythm, such as a cardiac cycle, as well as morphology of the pumping waveform and duration of each state of the pump. The waveform of the pump 34 and resulting oscillation or modulation of cerebrospinal fluid 18, can be consistent in time, frequency, magnitude, shape (ramp up/down), etc., or can have variations either in a fixed pattern, or include random variations in response to sensed conditions or changes thereof. The monitor or controller 36, can be connected to or include other controllers, monitors or equipment, such as standard hospital monitors and equipment. In addition, the monitor or controller can be a standard hospital monitor or equipment. If desired, the monitor or controller 36 can be incorporated or combined with the actuator 29.

The volume 17 can be sealed in manner that can prevent pathogens surrounding volume 17 from entering the sterile fluid space within the volume 17 and can allow a pressure and pumping action to be formed therein by actuator 29. The volume 17 can have openings in the seal configured to allow the insertion or withdrawal of fluid and still be considered sealed. Although a drainage bag 30 can be connected to the volume 17 via conduit 28, valve 26 and conduit 24, and form an opening into volume 17 which can allow insertion or withdrawal of fluid, these components can also be sterile and sealed so that pathogens do not enter the volume 17 from these components. In addition, components 30, 28, 26 and 24 do not prevent pressure and pumping action to be formed in volume 17. Pressure and pumping action of volume 17 can be aided, enabled, or enhanced by closing valve 26. In some embodiments, the catheter 20, volume 17 and drainage bag 30 together, or portions thereof, can form a sterilized disposable 9. Since the volume 17 can be fluidly sealed, the volume 17 can be connected to an unsterilized actuator 29, and being in fluid and sterile isolation from the actuator 29, provide drainage and oscillation of cerebrospinal fluid 18 in a sterile manner. In other embodiments, the actuator 29 can be sterile or sterilized and can be or form part of the volume 17.

Figure 2:
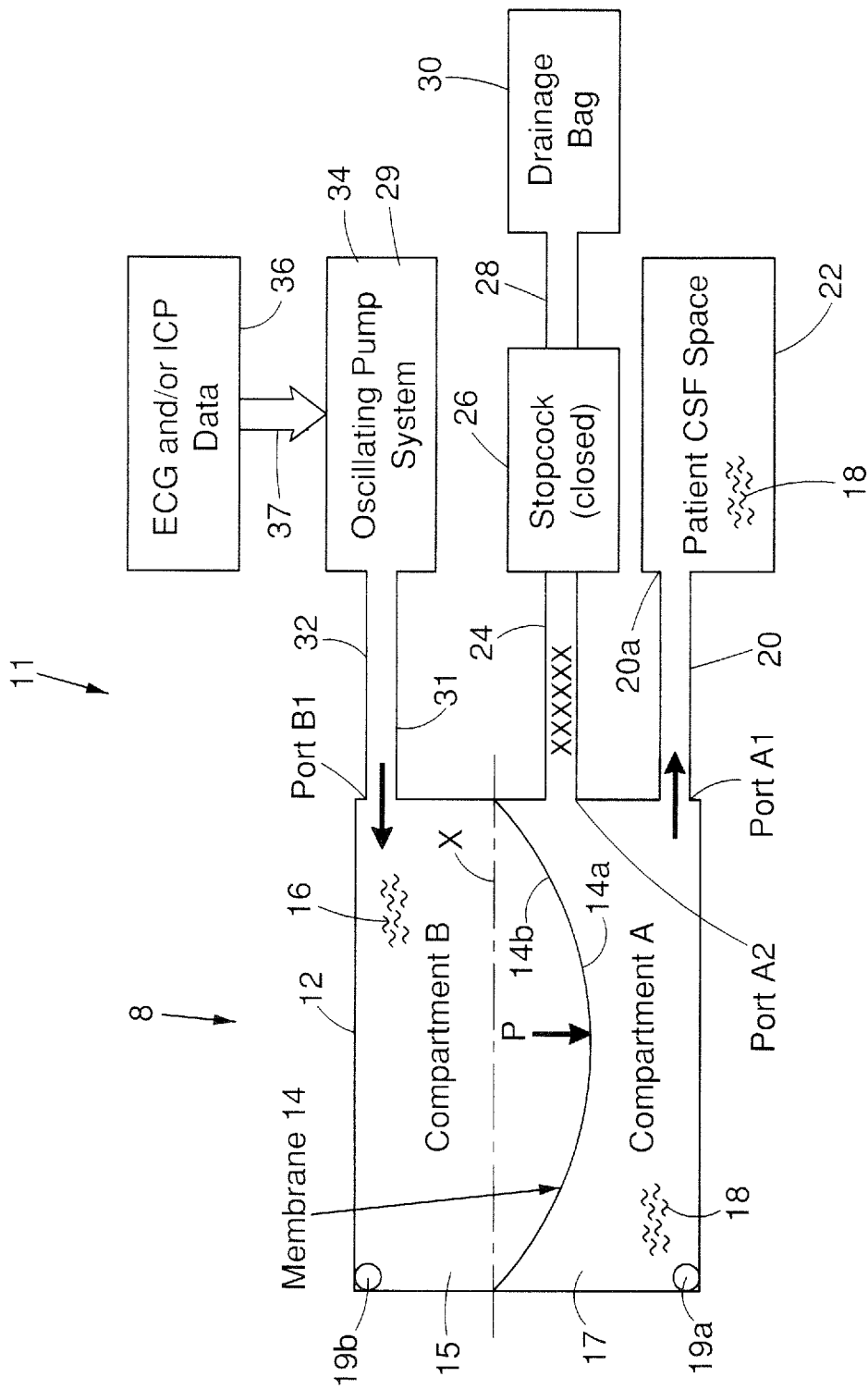
FIGS. 2 and 3 are schematic drawings of the operation of one embodiment of a device or system for regulating cerebrospinal fluid having an oscillating sealed fluid volume with a diaphragm.
Figure 3:
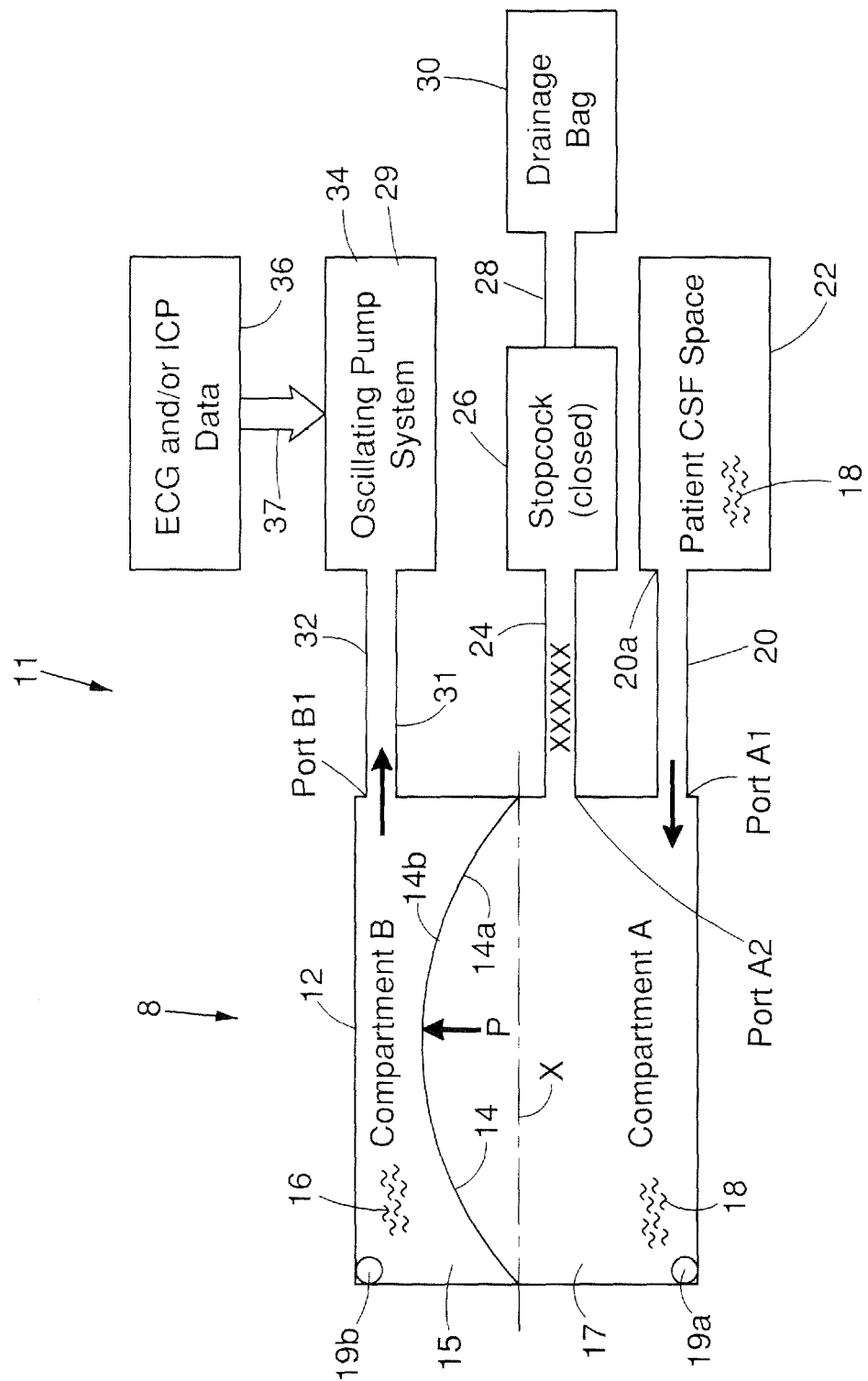

Referring to FIGS. 2 and 3, cerebrospinal fluid regulating device or system 11 is an embodiment of the present invention which has an actively oscillatably changeable sealed fluid volume 17 that is part of an oscillating or modulating fluid assembly 8, and can be positioned or located within an enclosed container or housing 12. The container 12 can be a rigid housing, tank or reservoir, or alternatively, a flexible bag. The container 12 can include a deformable membrane 14 separating the container 12 into two fluidly isolated and enclosed regions, changeable sealed volume 17 or compartment A, and actuation region 15 or compartment B. The deformable membrane 14 can have first 14a second 14b surfaces on opposite fluidly isolated sides that can form or define a boundary of at least a portion of volume 17, and region 15. The container 12 can form the remaining portions of volume 17 and region 15. The deformable membrane 14 can be fluid and biologically tight, and can be sealed or secured within container 12 in a fluid and biologically tight manner. The deformable membrane 14 can be sized, and/or formed of elastic material to enable movement to one side of a delineation axis X or to the other side of axis X, to alternately increase and decrease the volume sizes of volume 17 and region 15. For example, the deformable membrane 14 can be a flexible membrane having a surface area that is larger than the cross-section of the container 12, allowing the deformable membrane to move under an applied force to either side of axis X, and/or can be an elastic membrane, that can resiliently stretch or expand under an applied force to either side of axis X. In some embodiments, the deformable membrane 14 can be formed with a resilient bias, for example, biased for expanding into actuation region 15.

The container 12 can have three inlet/outlet ports A1, A2 and B1, Ports A1 and A2 can be in fluid communication with volume 17. Port A1 can be coupled to conduit or catheter 20, for example a ventricular drainage catheter, and can include additional tubing and fittings. Port A2 can be coupled to drainage bag 30 via conduit 24, and valve 26. Port B1 can be in fluid communication with actuation region 15 and connected to an oscillating or modulating pump or pump system 34 by a conduit 32.

The pump 34 can serve as an actuator 29 by pumping an actuation fluid 16, such as air or other gases, or a suitable liquid, to and from pump 34 and actuation region 15, through a conduit 32 that serves as a coupling member 31. Pump 34 can be a suitable pump such as a piston, rotary centrifugal, roller, peristaltic pump, etc. The actuation fluid 16 can be a biocompatible liquid such as saline.

Referring to FIG. 2, pumping of the actuation fluid 16 into the actuation region 15 of container 12 as shown by the arrow, can apply a force or fluid pressure P on the surface 14b of deformable membrane 14 which forces the deformable membrane 14 onto the compartment A side of axis X, thereby enlarging or increasing the fluid volume size of region 15 and decreasing the fluid volume size of volume 17. This forces cerebrospinal fluid 18 out of the volume 17 into catheter 20, as shown by the arrow, so that a certain volume of cerebrospinal fluid 18 can exit the distal end 20a of catheter 20 and enter cerebrospinal fluid space 22, which can increase fluid pressure therein.

Conversely, referring to FIG. 3, when pump 34 pumps actuation fluid 16 out of the actuation region 15 as shown by the arrow, this can create a suction or pressure drop within region 15 and can allow the deformable membrane 14 to be drawn onto the compartment B side of axis X, thereby decreasing the fluid volume size of region 15, while at the same time drawing cerebrospinal fluid 18 as shown by the arrow into and increasing the fluid volume size of volume 17. In some embodiments, fluid pressure P of cerebrospinal fluid 18 can act on surface 14a of deformable membrane 14. The increase in fluid volume size of volume 17 can create a suction within volume 17 and catheter 20, causing cerebrospinal fluid 18 in the cerebrospinal fluid space 22 to be drawn into the distal end 20a of the catheter 20, which can decrease or reduce fluid pressure in the cerebrospinal fluid space 22. The deformable membrane 14 can form a fluid and sterile or biological barrier which can allow volume 17 to be sterilized and continue to remain and operate in a sterile manner whether or not the pump 34 and actuation fluid 16 are sterile. The pump 34 can alternately physically squeeze or compress, and then expand the fluid volume size of volume 17.

The pump 34 can be controlled by monitor or controller 36 to oscillate or modulate actuation fluid 16 in and out of the actuation region 15, thereby oscillating or modulating the deformable membrane 14 and therefore cerebrospinal fluid 18, in and out of the cerebrospinal fluid space 22, which can oscillate or modulate fluid pressure therein. The monitor or controller 36 can be connected by control lines to any or all of sensors 13a, 21a, 35 and 25 as in FIG. 1. In addition, pressure sensors 19a and 19b can be positioned within volume 17 and actuation region 15 for monitoring the pressure of cerebrospinal fluid 18 and actuation fluid 16. Sensors 19a and 19b can be connected to monitor or controller 36 by physical or wireless control lines. The oscillation or modulation sequence, timing duration, magnitude, waveform, etc., can be affected by the pressures sensed by sensors 19a and 19b. The location of the sensors 19a and 19b can be varied, for example, can be located near ports A1 and B1, or in conduits 20 and 32. In some embodiments, sensors that sense volume can be employed, or sensors that sense a parameter associated with volume, for example, the position of deformable membrane 14. Although a pump 34 has been shown connected to actuation region 15 by a conduit 32, in other embodiments, a reciprocating piston of an actuator 29 can extend into region 15 for displacing the actuation fluid 16 and deformable membrane 14 in an oscillating or modulating manner.

Figure 4:
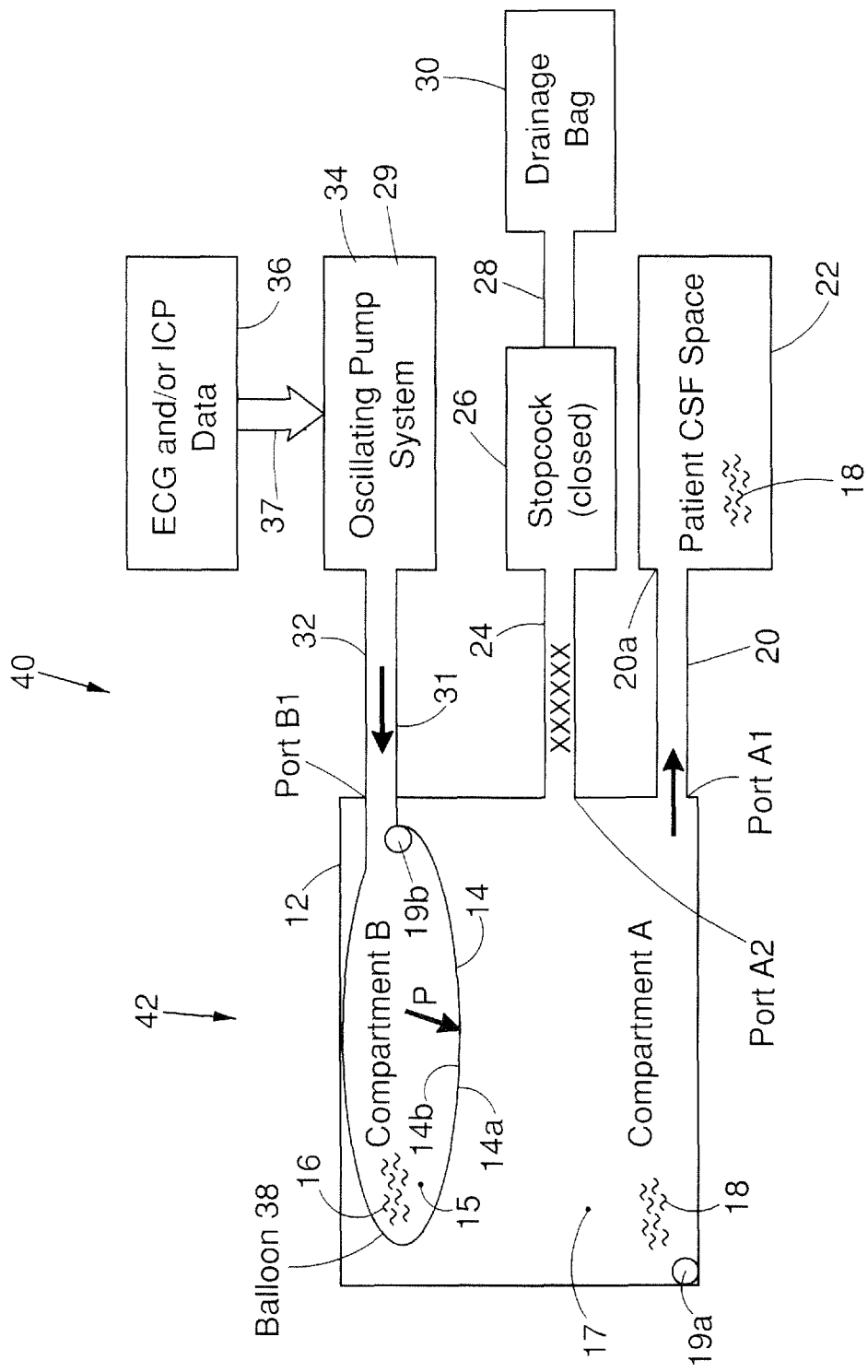
FIGS. 4 and 5 are schematic drawings of another embodiment of a device or system for regulating cerebrospinal fluid having an oscillating sealed fluid volume with a balloon.
Figure 5:
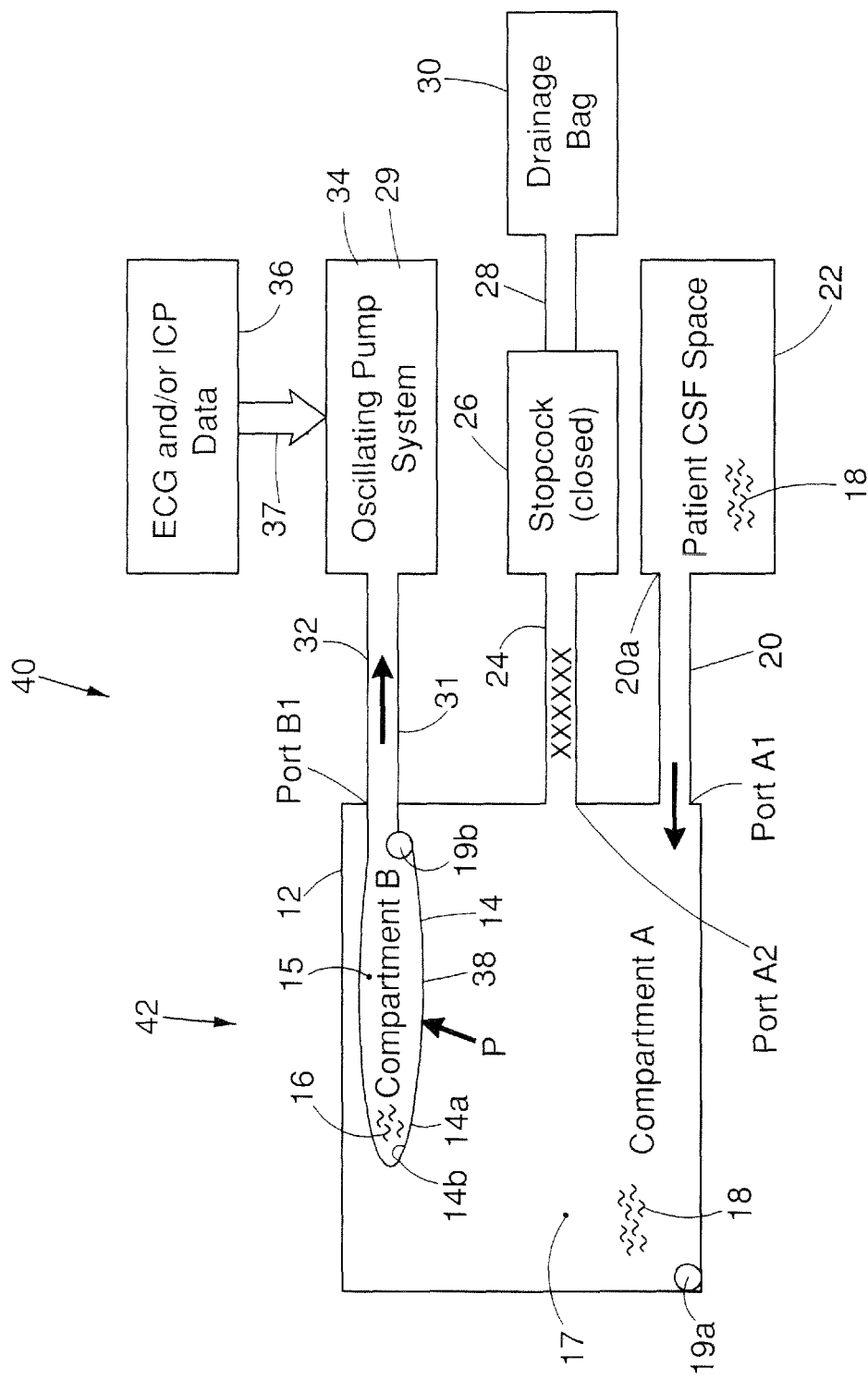

Referring to FIGS. 4 and 5, cerebrospinal fluid regulating device or system 40 differs from device 11 in that oscillating or modulating fluid assembly 42 is employed in place of oscillating fluid assembly 8. Assembly 42, as with assembly 8, also includes a container or housing 12 with ports A1, A2 and B1. A deformable membrane 34 in the shape or configuration of a bag, bladder or balloon 38 can be positioned within container 12, and connected and sealed in a fluid tight manner in fluid communication with port B1 for fluid communication with pump 34 via conduit 32. The interior of balloon 38 can form actuation region 15, and the areas within container 12 outside balloon 38 can form volume 17. Balloon 38 can be a fluid and sterile or biologically tight barrier, and the interior, fluidly and biologically isolated from volume 17, to allow volume 17 to be sterilized and remain sterile. Balloon 38 can be formed of resilient or stretchable material, but alternatively, can be non stretchable. Pumping of actuation fluid 16 into and out of the balloon 38 by pump 34 can expand and deflate balloon 38 to increase and decrease the fluid volume size of balloon 38.

Referring to FIG. 4, pumping actuation fluid 16 into balloon 38 and actuation region 15 as shown by the arrow, can apply a force or fluid pressure P on surface 14b on the interior of balloon 38. Since surface 14b is the inner surface of balloon 38, the balloon 38 expands in volume size within the container 12. The volume 17 is in the regions of container 12 not occupied by balloon 38, so that as balloon 38 expands, volume 17 decreases in fluid volume size, which forces cerebrospinal fluid 18 out of volume 17 into catheter 20, and out the distal end 20a into cerebrospinal space 22, as shown by the arrow, which can increase fluid pressure therein.

Conversely, referring to FIG. 5, pumping actuation fluid 16 out of balloon 38 and actuation region 15 as shown by the arrow, can create a suction or pressure drop within the balloon 38 and against surface 14b, which causes or allows collapse or deflation of the balloon 38, thereby decreasing the internal fluid volume size of the balloon 38 and actuation region 15. The fluid pressure P of cerebrospinal fluid 18 within volume 17 on the exterior of balloon 38 on the surface 14a, can also aid in the collapse of balloon 38. As balloon 38 and actuation region 15 decreases in fluid volume size within container 12, the fluid volume size of volume 17 increases and can create a suction within volume 17 and catheter 20, drawing cerebrospinal fluid 18 into volume 17 as shown by the arrow, causing cerebrospinal fluid 18 in the cerebrospinal fluid space 22 to be drawn into the distal end 20a of catheter 20, which can decrease or reduce the fluid pressure in the cerebrospinal fluid space 22. Device 40 can be operated and controlled in a similar manner as device 11.

Referring to FIG. 6, in other embodiments, actively oscillatable changeable sealed fluid volume 17 can be incorporated in a bellows device 50 which can have a collapsible and expandable bellows membrane 54 extending or positioned between pivoting arms 52. The membrane 54 can extend between and be fluidly sealed to the arms 52 to form volume 17 in the space therebetween, or can be a flexible fluid and biological tight container or bag forming volume 17, positioned between and connected to arms 52. The membrane 54 can include ports A1 and A2 for connection to catheter 20 and drainage bag 30. Movement of the arms 52 towards and away from each other as indicated by the arrow can increase and decrease the fluid volume size of volume 17 to cause oscillation or modulation of cerebrospinal fluid 18. The arms 52 can pivot about a pivot point 56, and can be moved in an arc by actuator 29 via coupling member 31. The actuator 29 can be for example, a rotary motion actuator, such as a servomotor coupled to the pivot point 56, or a linear actuator such as a piston or fluid cylinder coupled to, at least one arm 52. Actuator 29 can also be other suitable types of actuating devices. Bellows device 50 can be a disposable unit or can be a permanent unit that is sterilized.

Referring to FIG. 7, bellows device 60 is another embodiment which differs from bellows device 50 in that collapsible and expandable bellows membrane 64 is positioned between members 62 that can move linearly towards and away from each other as indicated by the arrows for increasing and decreasing the fluid volume size of volume 17. Membrane 64 can be sealed to members 62 or can be a bag connected to members 62. Actuator 29 can be connected to bellows device 60 by coupling member 31 for moving members 62 relative to each other. Actuator 29 can be a linear motion actuator. In some embodiments of FIGS. 6 and 7, the membranes 54 or 64, in a bag configuration, can be sterile disposables and can be attachable between arms 52 or members 62. In other embodiments, the arms 52 or members 62 and the membranes 54 or 64, can form sterile disposable units that can be connected to actuator 29. In addition, the actuator 29 can be part of the bellows devices 50 or 60.

Referring to FIG. 8, oscillating or modulating fluid assembly 70 is an embodiment that differs from assembly 8 in that a reciprocating piston 72 is positioned and movably or slidably sealed within container 12. Piston 72 can be fluidly sealed to the interior walls of container 12 with a sliding seal 74. The container 12 and piston 72 can be cylindrical, and the sliding seal 74 can be an annular sealing ring positioned within an annular groove. If desired, more than one seal 74 can be employed, or other suitable sealing configurations. When actuation fluid 16 is pumped by pump 34 into actuation region 15, the piston 72 moves, increasing the fluid volume size of actuation region 15 and decreasing the fluid volume size of volume 17, thereby delivering cerebrospinal fluid 18 into cerebrospinal fluid space 22, which can increase fluid pressure therein. Conversely when pump 34 pumps actuation fluid 16 out of region 15, the piston 72 moves to decrease the fluid volume size of region 15 and increases the fluid volume size of volume 17, thereby removing cerebrospinal fluid 18 from cerebrospinal fluid space 22, which can decrease or reduce fluid pressure therein. Oscillation or modulation of cerebrospinal fluid 18 fluid pressure can be achieved by reciprocating piston 72.

Referring to FIG. 9, oscillating or modulating fluid assembly 75 is an embodiment that differs from assembly 70 in that reciprocating piston 72 can be connected to an actuator 29 by a mechanical coupling member 31, such as a reciprocating coupling rod for mechanically driving or moving the piston 72 in an oscillating or modulating manner. The actuator 29 can be a linear motion device, such as a fluid cylinder, or can be a motor which in conjunction with the coupling member 31 and the piston 72, can form a crank slider mechanism. In some embodiments, the actuator 29 and coupling rod can be incorporated into or mounted on container 12.

Referring back to FIGS. 1-3, an example of operation of an embodiment of device 11 now follows. A patient undergoes catherization for removal of cerebrospinal fluid 18 for purposes of relieving pressure and increasing cerebral blood flow, and/or for monitoring the cerebrospinal fluid 18. The catheter 20 is inserted into the cerebrospinal fluid space 22. If the catheter 20 is separate or separated from the container 12, the catheter 20 can be secured to port A1. If desired, a ligature can be used. Likewise if the drainage bag 30 is separate or separated, the drainage bag 30 and valve 26 can be connected to port A2 via conduit 24. Compartment A or volume 17 can then be filled with cerebrospinal fluid 18 from cerebrospinal fluid space 22. If desired, valve 26 can opened to drain cerebrospinal fluid 18 into drainage bag 30, and then closed. If there is not sufficient cerebrospinal fluid 18 to fill volume 17, saline solution can be used to fill volume 17. Fluid within the volume 17, whether cerebrospinal fluid 18, saline or both, is considered cerebrospinal fluid for purposes of describing operation of the devices in the present invention. When pump 34 is separate from container 12, pump 34 can be connected to port B1 via conduit 32. An ECG signal from a standard monitoring system in the hospital, or an independently placed ECG monitory system can be obtained from the patient, for example from sensor 35 (FIG. 1). In addition, a signal can be obtained which is related to intracranial pressure (ICP) from a standard intracranial pressure monitor used in a hospital, or a pressure sensing system placed in compartment A and/or the tubing attached to compartment A, such as with sensors 25 (FIGS. 1) and 19a. One or both of the ECG and ICP signals can be used by controller 36 to regulate the movement of pump 34, and change the ICP pressure if appropriate, via modulation of actuation fluid 16 in actuation region 15, and the deformable membrane 14 located between actuation region 15 and volume 17. Actuation fluid 16 can be removed from actuation region 15 or compartment B during systoli, and added during diastoli. Modulation can be based on the cardiac cycle, respiratory cycle, ICP and/or CSF pressure monitoring, cerebral blood flow monitory, other suitable biorhythms that can have a relation to ICP, or other after standard intensive care unit monitoring systems. Device 11 can be used in an intermittent or continuous fashion, and can be used during drainage of cerebrospinal fluid 18. Devices 10 and 40 can be used similarly.

The devices in the present invention can be used for treating patients having altered intracranial compliance, decreased cerebral blood flow and/or abnormal intracranial pressure. Such conditions can occur with head injuries, aging, cerebrovascular disease, brain atrophy, post brain hemorrhage and infection, vasospasms, congestive heart failure, carotid endarterectomy, carotid occlusion/stenosis, cardiopulmonary bypass procedure, hydrocephalus, stroke, dementia, or migraine headaches. Hydrocephalus can be chronic hydrocephalus, normal pressure hydrocephalus, pseudotumor, cerebri, or slit ventricle syndrome. Stroke can be acute stroke, chronic stroke, microvascular disease, dementia, moya-moya, multiple infarct disease, posterior circulation insufficiencies or Binswanger disease. Dementia can be vascular dementia, Alzheimer's disease, and normal pressure hydrocephalus. Migraine headaches can be pediatric migraines, adult migraines, or intractable migraines. In some conditions, increased intracranial pressure may be desired. Depending upon the condition, treatment can be temporary or long term.

While this invention has been particularly shown and described with references to example embodiments thereof, it will be understood by those skilled in the art that various changes in form and details may be made therein without departing from the scope of the invention encompassed by the appended claims.

For example, embodiments of the present invention can be used for draining, adding and/or oscillating fluid in other spaces, cavities, or fluid systems of a patient. In addition, features of the various embodiments shown and described can be combined together, or some features can be omitted.

What is claimed is:

1. A device for regulating cerebrospinal fluid in a cerebrospinal fluid space comprising:
   a cerebrospinal conduit having a distal end for insertion into the cerebrospinal fluid space in fluid communication with the cerebrospinal fluid;
   an actively oscillatably changeable sealed fluid volume in fluid communication with the cerebrospinal conduit, the changeable sealed fluid volume being within an enclosed container, the container containing at least one of cerebrospinal fluid and saline fluid therein, a deformable fluid tight balloon having interior and exterior surfaces extending into the container, the balloon for expanding and deflating in volume size within the container for decreasing and increasing fluid volume size of the changeable sealed fluid volume, the container having a first port in communication with the changeable sealed fluid volume, the cerebrospinal conduit being coupled to the first port of the container, the changeable sealed fluid volume being in a sealed fluid path extending to the distal end of the cerebrospinal conduit and capable of actively oscillating in a changing fluid volume size for oscillating the cerebrospinal fluid in and out of the distal end of the cerebrospinal conduit and cerebrospinal fluid space; and
   pressure sensor elements positioned for sensing pressure within the chanegable sealed fluid volume and within the balloon for controlling oscillation parameters for oscillating the cerebrospinal fluid.

2. The device of claim 1 further comprising an actuator coupled to the changeable sealed fluid volume for oscillating the changing fluid volume size of the changeable sealed fluid volume.

3. The device of claim 2 further comprising a sensor system for sensing conditions of a patient, the sensor system being in communication with the actuator for controlling operation of the actuator.

4. The device of claim 3 in which the sensor system includes a control system for controlling operation of the actuator.

5. The device of claim 4 in which the operation of the actuator is synchronized with a biorhythm of the patient.

6. The device of claim 5 in which the biorythm is related to the patient's heart.

7. The device of claim 5 in which the actuator is synchronized with a signal that is selected from the group consisting of an ECG signal, a pulse signal and a pressure signal.

8. The device of claim 4 in which the sensor system includes a sensor for sensing within the cerebrospinal fluid space for forming a feed back loop to control the level of cerebrospinal fluid within the cerebrospinal fluid space.

9. The device of claim 1 further comprising a fluid storage container coupled to the changeable sealed fluid volume and controllably fluidly isolated from the changeable sealed fluid volume.

10. The device of claim 1 in which application of an oscillating force on the interior surface of the balloon is capable of deforming the balloon to oscillate the changing fluid volume size of the changeable sealed fluid volume.

11. The device of claim 10 in which the container has a second port in communication with the interior surface of the balloon.

12. The device of claim 11 further comprising an oscillating pump coupled to the second port of the container for providing oscillating fluid pressure to the interior surface of the balloon.

13. A device for regulating cerebrospinal fluid in a cerebrospinal fluid space comprising:
   a cerebrospinal conduit having a distal end for insertion into the cerebrospinal fluid space in fluid communication with the cerebrospinal fluid; and
   an actively oscillatably changeable sealed fluid volume in fluid communication with the cerebrospinal conduit, the changeable sealed fluid volume being within an enclosed container, the container containing at least one of cerebrospinal fluid and saline fluid therein, a deformable fluid tight balloon having interior and exterior surfaces extending into the container, the balloon for expanding and deflating in volume size within the container for decreasing and increasing fluid volume size of the changeable sealed fluid volume, the container having a first port in communication with the changeable sealed fluid volume, the cerebrospinal conduit being coupled to the first port of the container, the changeable sealed fluid volume being in a sealed fluid path extending to the distal end of the cerebrospinal conduit and capable of actively oscillating in a changing fluid volume size for oscillating the cerebrospinal fluid in and out of the distal end of the cerebrospinal conduit and cerebrospinal fluid space;
   an actuator coupled to the changeable sealed fluid volume for oscillating the changing fluid volume size of the changeable sealed fluid volume;
   a control system for controlling operation of the actuator synchronized with a biorhythm; and
   pressure sensor elements positioned for sensing pressure within the changeable sealed fluid volume and within the balloon for controlling oscillation parameters for oscillating the cerebrospinal fluid.

* * * * *